US006473487B1

(12) United States Patent
Le (10) Patent No.: US 6,473,487 B1
(45) Date of Patent: Oct. 29, 2002

(54) METHOD AND APPARATUS FOR PHYSICAL CHARACTERISTICS DISCRIMINATION OF OBJECTS USING A LIMITED VIEW THREE DIMENSIONAL RECONSTRUCTION

(75) Inventor: Khai Minh Le, Huntington Beach, CA (US)

(73) Assignee: Rapiscan Security Products, Inc., Hawthorne, CA (US)

(*) Notice: Subject to any disclaimer, the term of this patent is extended or adjusted under 35 U.S.C. 154(b) by 0 days.

(21) Appl. No.: 09/752,811

(22) Filed: Dec. 27, 2000

(51) Int. Cl.$^7$ ............................................... G01N 23/04
(52) U.S. Cl. ............................................. 378/57; 378/9
(58) Field of Search ........................... 378/57, 53, 54, 378/92, 9, 4, 15, 98.9

(56) References Cited

U.S. PATENT DOCUMENTS

| 3,581,087 A | 5/1971 | Brinkerhoff et al. ........ 250/51.5 |
| 3,884,816 A | 5/1975 | Takahashi ................... 250/359 |
| RE28,544 E | 9/1975 | Stein et al. ................. 250/369 |
| 3,924,064 A | 12/1975 | Nomura et al. .............. 178/6.8 |
| 4,075,492 A | 2/1978 | Boyd et al. ................. 250/445 |

(List continued on next page.)

FOREIGN PATENT DOCUMENTS

WO   WO 92/02892   2/1992   ........... G06F/15/52

OTHER PUBLICATIONS

PerkinElmer Instruments, "Z-Scan7", printed from http://instruments.perkinelmer.com/products/catalog/products/prod81.asp on Aug. 4, 2000 (3 pages).

Technical Digest Image Processing for 2–D and 3–D Reconstruction from Projections: Theory andPractice in Medicine and the Physical Sciences.

"Passenger Screening Technologies", Airline Passenger Security Screening, pp. 13–21.

Alvarez, et al., "Energy–Selective Reconstructions in X–ray Computerized Tomography", 1976, Phys. Med. Biol., vol. 21, No. 5, pp. 733–744.

Bossi et al., "Backscatter X–Ray Imaging", Oct. 1988, Materials Evaluation, vol. 46.

Ellenbogen, Mike, "Checking in with New Bomb Detection Strategies", printed from http://www.securityman...om/library/000190.html on Dec. 1, 1996, 6 pages.

Gregory, William, Medical X–Ray Measuring Device Finds Use in Explosive Detection:, Apr. 28, 1986, Aviation Week & Space Technology, vol. 124, No. 17.

Rutt, Brian, "Split–Filter Computed Tomography: A Simple Technique for Dual Energy Scanning", pages J. 1980, Comput. Assist. Tomogr., vol. 4, No. 4, pp. 501–509.

*Primary Examiner*—David P. Porta
(74) *Attorney, Agent, or Firm*—Thelan Reid & Priest LLP; Thierry Lo (57) ABSTRACT

A method and apparatus for determining a specified physical characteristic in an object exposes the object to at least two angularly fixed sources of electromagnetic radiation to create projected images of the object. The sources are rotationally scanned about the object so as to oscillate in an angular range about the object. The sources are relatively stationary to one another. A three dimensional reconstructed image of the object based on the projected images of the object is created and examined for a specified physical characteristic in the object.

64 Claims, 10 Drawing Sheets

U.S. PATENT DOCUMENTS

| | | | | |
|---|---|---|---|---|
| 4,138,721 | A | 2/1979 | Boyd | 364/414 |
| 4,174,481 | A | 11/1979 | Liebetruth | 250/445 |
| 4,196,352 | A * | 4/1980 | Berninger et al. | 378/10 |
| 4,228,353 | A | 10/1980 | Johnson | 250/356 |
| 4,267,446 | A | 5/1981 | Brown et al. | 250/255 |
| 4,298,800 | A | 11/1981 | Goldman | 250/445 |
| 4,303,830 | A * | 12/1981 | Heinzelmann et al. | 378/4 |
| 4,426,721 | A | 1/1984 | Wang | 378/99 |
| 4,472,822 | A | 9/1984 | Swift | 378/10 |
| RE32,164 | E | 5/1986 | Kruger | 378/19 |
| 4,637,040 | A | 1/1987 | Sohval et al. | 378/9 |
| RE32,779 | E | 11/1988 | Kruger | 378/19 |
| 4,783,794 | A | 11/1988 | Dietrich | 378/57 |
| 4,809,312 | A | 2/1989 | Annis | 378/146 |
| 4,821,306 | A | 4/1989 | Mulder | 378/156 |
| 4,825,454 | A | 4/1989 | Annis et al. | 378/87 |
| 4,841,554 | A | 6/1989 | Doenges et al. | 378/57 |
| 4,899,283 | A | 2/1990 | Annis | 364/413.15 |
| 4,958,363 | A | 9/1990 | Nelson et al. | 378/85 |
| 5,073,782 | A | 12/1991 | Huguenin et al. | 342/179 |
| 5,179,581 | A | 1/1993 | Annis | 378/57 |
| 5,181,234 | A | 1/1993 | Smith | 378/87 |
| 5,227,800 | A | 7/1993 | Huguenin et al. | 342/179 |
| 5,247,561 | A | 9/1993 | Kotowski | 378/87 |
| 5,349,191 | A | 9/1994 | Rogers | 250/367 |
| 5,432,234 | A | 7/1995 | Nelson et al. | 250/208.1 |
| 5,442,672 | A | 8/1995 | Bjorkholm et al. | 378/4 |
| 5,479,023 | A | 12/1995 | Bartle | 350/390.04 |
| 5,481,584 | A | 1/1996 | Tang et al. | 378/98.9 |
| 5,490,196 | A | 2/1996 | Rudich et al. | 378/101 |
| 5,490,218 | A | 2/1996 | Krug et al. | 382/100 |
| 5,600,700 | A | 2/1997 | Krug et al. | 378/57 |
| 5,642,393 | A | 6/1997 | Krug et al. | 378/57 |
| 5,699,400 | A | 12/1997 | Lee et al. | 378/57 |
| 5,712,926 | A | 1/1998 | Eberhard et al. | 382/205 |
| 5,812,630 | A | 9/1998 | Blaffert | 378/83 |
| 5,838,758 | A | 11/1998 | Krug et al. | 378/53 |
| 5,870,449 | A | 2/1999 | Lee et al. | 378/57 |
| 5,901,198 | A | 5/1999 | Crawford et al. | 378/57 |
| 5,917,880 | A | 6/1999 | Bjorkholm | 378/57 |
| 5,940,468 | A | 8/1999 | Huang et al. | 378/57 |
| 5,966,422 | A * | 10/1999 | Dafni et al. | 378/15 |
| 5,974,111 | A | 10/1999 | Krug et al. | 378/57 |
| 6,018,562 | A * | 1/2000 | Willson | 378/57 |
| 6,078,642 | A | 6/2000 | Simanovsky et al. | 378/57 |
| 6,081,580 | A | 6/2000 | Grodzins et al. | 378/87 |
| 6,088,423 | A | 7/2000 | Krug et al. | 378/57 |
| 6,094,472 | A | 7/2000 | Smith | 378/86 |

* cited by examiner

METHOD AND APPARATUS FOR PHYSICAL CHARACTERISTICS DISCRIMINATION OF OBJECTS USING A LIMITED VIEW THREE DIMENSIONAL RECONSTRUCTION

FIELD OF THE INVENTION

The present invention relates to the discrimination of physical characteristics of objects. More particularly, the present invention relates to a scanning system used to detect explosives or drugs and other items in baggage using a limited view three-dimensional reconstruction.

BACKGROUND OF THE INVENTION

Projection radiography has long been used for detection of metallic contraband in baggage. In general, X-rays may be used in projection radiography to measure the Compton scattering effects and photoelectric absorption to determine the number of electrons and the effective atomic number, respectively, of an object.

Figure 1A:
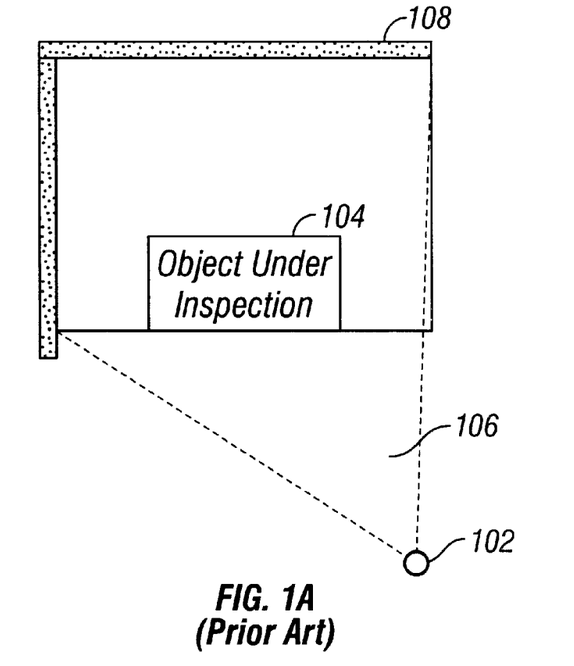
FIG. 1A is a schematic diagram of a side view of a conventional projection radiographic system having one x-ray source.

An example of a conventional projection radiography system is shown in FIG. 1A. The conventional projection radiography system includes an X-ray tube source 102, mounted in a suitable housing, to emit X-ray radiation toward an object 104 under inspection. A beam 106 passes through object 104 and hit a conventional X-ray screen 108 of suitable phosphorescent material.

Object 104 is supported on a conveyor belt (not shown) that moves successive portions of the object through beam 106 such that successive slices of the object are scanned by beam 106. Mounted opposite light emitting screen 108 is a photo-detector array (not shown) that may comprise a linear array of photo-diodes (not shown) positioned coextensively beneath screen 108. When X-ray photons strike screen 108, screen 108 emits light in accordance with the energy and number of X-ray photons, which depend upon the characteristics of the portion of object 104 through which the X-ray ray photons pass. The photo-diodes receive light generated by contiguous portions of screen 108, and each photo-diode generates an electrical charge in accordance with the intensity of the light received thereby.

The conventional system described above is effective in detecting materials that have a high radiographic contrast, such as metallic objects. However, organic materials that have a low radiographic contrast, such as explosives, drugs, etc., are more difficult to detect with the conventional system. Moreover, such organic materials do not necessarily have a regular shape that would otherwise aid identification.

Dual energy detection systems have been developed which can detect organic materials. In a dual energy system, two X-ray beams having characteristically different photon energies are used. Typically, organic materials tend to transmit approximately the same amount of high energy and low energy X-rays. Metals, on the other hand transmit different amount of high energy and low energy X-ray. The amount of organic material present can therefore be determined.

Figure 1B:
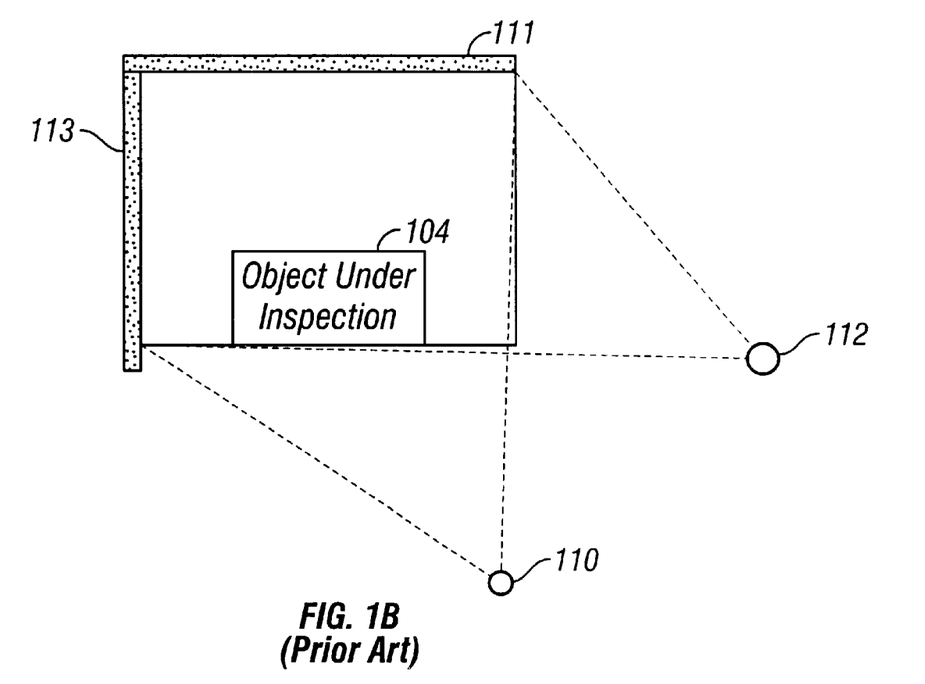
FIG. 1B is a schematic diagram of a side view of a conventional projection X-ray device having two x-ray sources and two detector systems.

Other dual energy detection systems, as illustrated in FIG. 1B, use two X-ray sources 110 and 112 positioned at distinct locations around object 104. For each x-ray source, there exist a corresponding detector system 111 and 113. The fan shape x-ray projection of both first and second sources intersects at object 104. By capturing different views of the projected image of object 104, an algorithm can be used to reconstruct a three-dimensional image of the object.

Figure 1C:
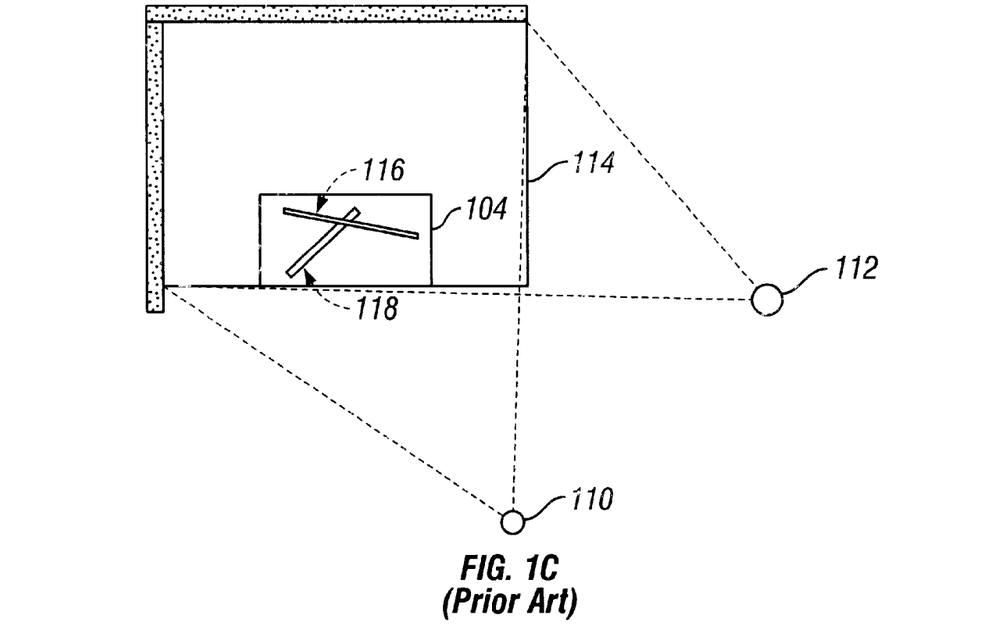
FIG. 1C is a schematic diagram of a side view of a conventional projection X-ray device with two x-ray sources and two detector systems examining a parcel containing several thin explosive sheets.

In a conventional dual energy projection system, however, as well as in the single energy projection system described above, the only characteristics that can be determined are line of sight characteristics, such as the projected number of electrons and the effective atomic number along the line of sight through the object. For example, a particular high measurement of N electrons/cm$^2$ along the line of sight could be created by either a very thin object of high density or by a relatively thick object of low density. Similarly, a measurement of an effective atomic number along the line of sight appropriate to aluminum could be caused by a plate of aluminum or by a slab of explosives coupled with a thin foil of iron. Such limited view reconstructions have serious deficiencies when called upon to detect a sheet of explosives. FIG. 1C illustrates the problem with projection imaging. A baggage scanning system has two x-ray sources 110 and 112. An enclosure 114 contains object 104 to be examined. Object 104 is, for example, a parcel or a piece of luggage containing several thin sheets of explosives 116 and 118. Unless sheet of explosives 116 is lined up to a very small angle relative to the X-ray beam as the position of x-ray source 112, its density projection spreads out so that it is overwhelmed by clutters of other objects (not shown) in object 104. Sheet explosive 116 can only be resolved by x-ray source 112. On the other hand, sheet explosive 118 cannot be resolved by either source. Thus, projection imaging alone is reliable to detect sheet explosives.

Figure 1D:
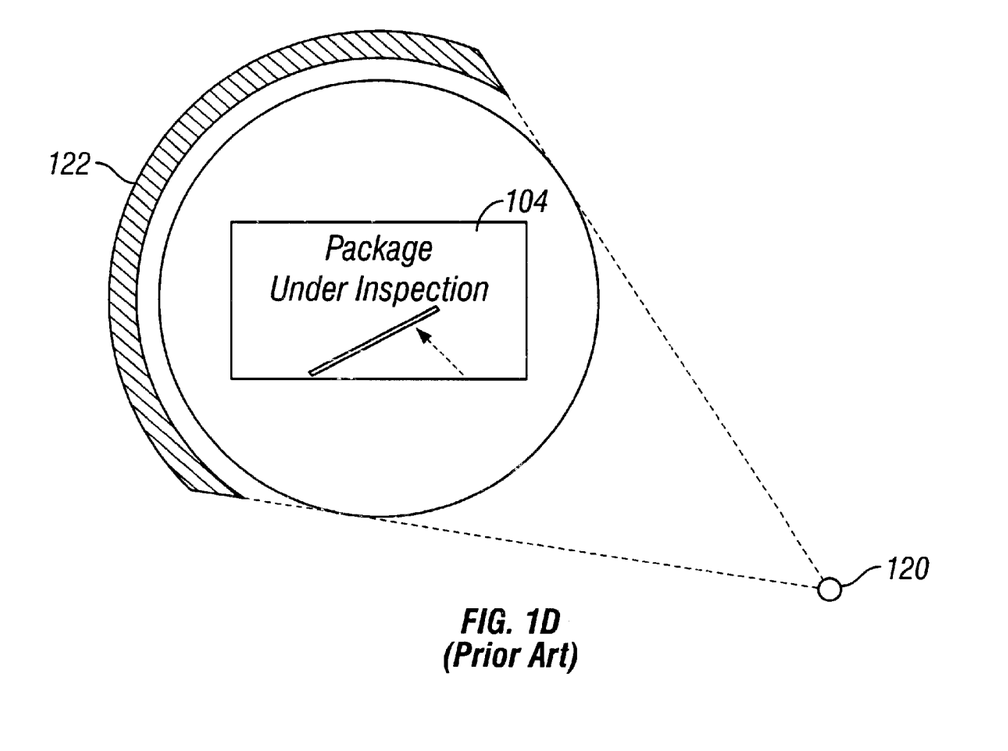
FIG. 1D is a schematic diagram of a side view of a conventional computerized tomography scanner.

Conventional computerized tomography, such as illustrated in FIG. 1D, can overcome the problems described above associated with conventional projection radiography using both single and dual energy X-rays. That is, the three-dimensional nature of the reconstructed image generated by computerized tomography removes many of the problems associated with projection radiography and permits an absolute determination of electron densities and atomic numbers. However, conventional computerized tomography requires many views over 180 degrees of rotation about the object being scanned in order to generate a high quality reconstructed image. That is, for each cross-sectional view or slice of the object, the X-ray source must be positioned at a relatively large number of locations about the object and at each location the object is exposed and a projection (i.e., a shadow of the object) of the object is measured. Conventional computerized tomography is therefore expensive, time consuming, and requires physically large and expensive hardware. Such equipment can cost $500,000 to $1,000,000 or more per unit.

To practically implement a nationwide or worldwide system of airport baggage scanners employing three-dimensional image reconstruction to more reliably detect contraband, weapons and dangerous materials requires a less expensive and more physically compact approach. Many units will be required to process streams of baggage quickly enough so that flights are not unduly delayed by the system. The units need to be reasonably affordable to the airlines that will buy them and the equipment must reasonably fit in available space in existing airports.

BRIEF DESCRIPTION OF THE INVENTION

A method and apparatus for determining a specified physical characteristic in an object exposes the object to at least two angularly fixed sources of electromagnetic radiation to create projected images of the object. The sources are rotationally scanned about the object so as to oscillate in an angular range about the object. The sources are relatively stationary to one another. A three dimensional reconstructed image of the object based on the projected images of the object is created and examined for a specified physical characteristic in the object.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings.

DETAILED DESCRIPTION

Embodiments of the present invention are described herein in the context of a method and apparatus for physical characteristics discrimination of objects using a limited view three-dimensional reconstruction. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 2:
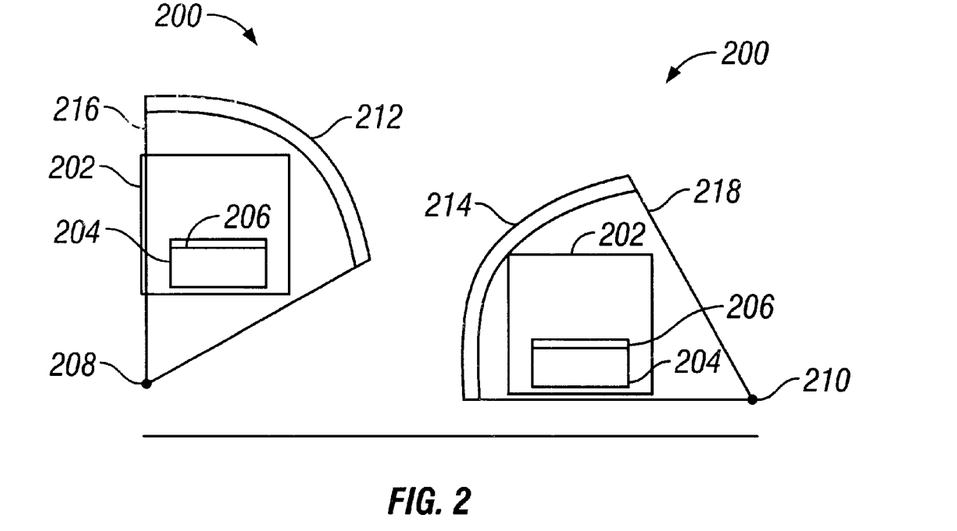
FIG. 2 is a schematic diagram of a side view of a projection radiographic system in accordance with one aspect of the present invention.

FIG. 2 is a schematic diagram of a side view of a projection radiographic system in accordance with one aspect of the present invention. A projection radiographic system 200 having a physical boundary, such as an inspection tunnel 202, is used for determining a specified physical characteristic in an object 204 placed therein. Object 204, for example, may be a parcel, or a piece of luggage, or any object which may fit into the physical boundary of projection radiographic system 200. Object 204 may lay flat or upright on a moving mechanism, such as a conveyor belt, that transports object 204 through projection radiographic system 200. Object 204 contains, for example, an organic or metallic material 206 such as contraband comprising thin sheets of explosives or thin sheets of drugs. As object 204 travels through projection radiographic system 200, at least two sources of electromagnetic radiation, such as x-ray sources 208 and 210, expose object 204 and material 206 to create projected images on screens 212 and 214. Some specified or predetermined physical characteristic of material 206 within object 204 may be, for example, the density of an explosive, the Z number of explosive, or the shape of the contraband with respect to its density as x-ray sources 208 and 210 move around material 206.

Both x-ray sources 208 and 210 may be located at different positions around object 204 to create several views of the projected images of object 204 and material 206. Sources 208 and 210 are relatively stationary to each other so that their respective projected images stay fixed in relation to each other. In accordance with an embodiment of the present invention, a three dimensional image of material 206 within object 204 is created by generating a contiguous series of slices of object 204. The three dimensional image is preferably a representation of the density of object 204 in units of grams/cm$^3$ or a material type in terms of a Z-number. Each slice is a reconstructed cross-sectional view of object 204 generated from the two view X-ray projections 212 and 214 taken at cross-section. X-ray sources 208 and 210 emit a fan shaped beams of X-rays 216 and 218 respectively which are transmitted through object 204 to create a two-dimensional projected image that is detected by two array of sensors, such as photodetectors behind screen 212 and 214. The screens preferably include a large number of sensors uniformly distributed along a line that is aligned with fan shaped beam 216 and 218. There may be one screen for each x-ray source.

Figure 3A:
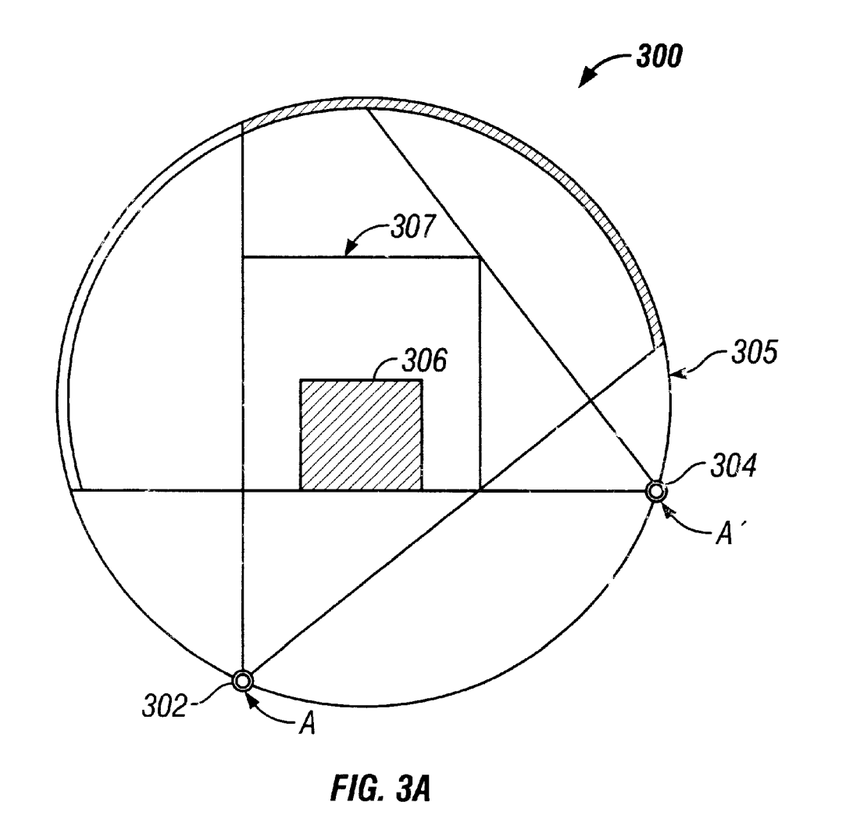
FIG. 3A is a schematic diagram of a side view of a projection radiographic system illustrating an example of a position of the X-ray sources in accordance with one aspect of the present invention.
Figure 3B:
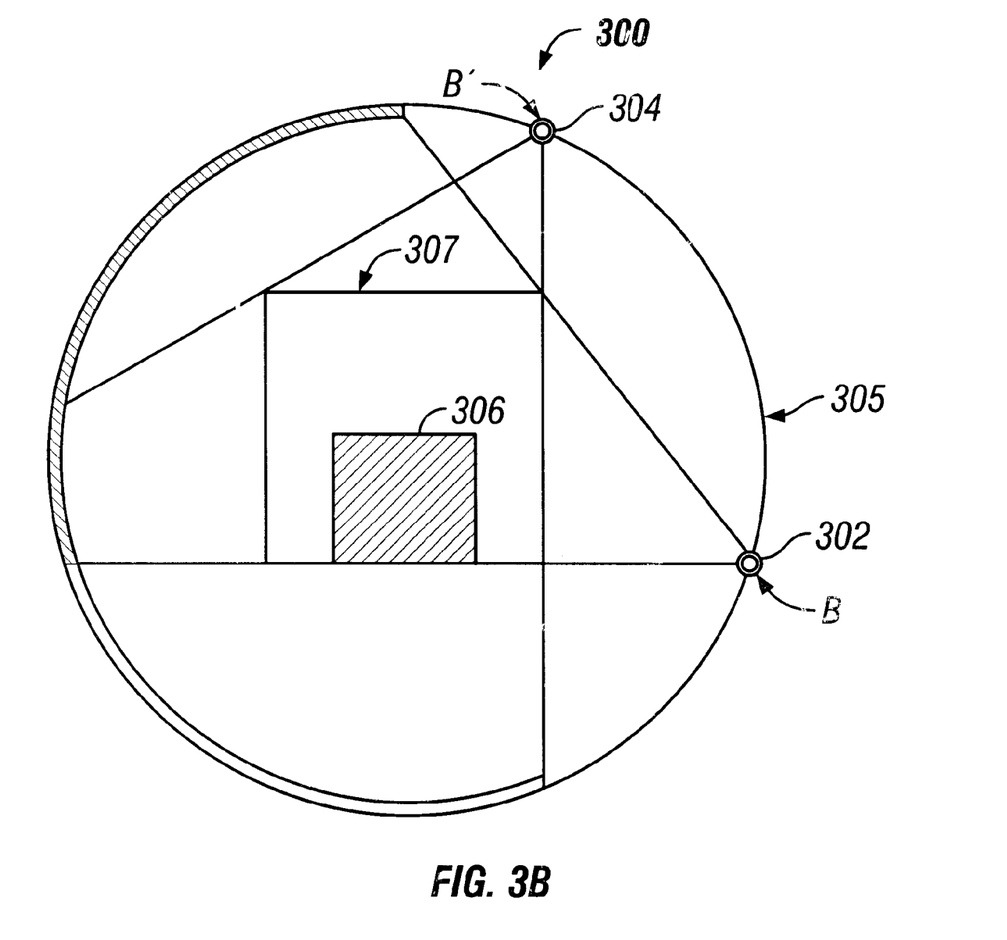
FIG. 3B is a schematic diagram of a side view of a projection radiographic system illustrating another example of a position of the X-ray sources in accordance with one aspect of the present invention.

FIGS. 3A and 3B illustrate schematic diagrams of a projection radiographic system illustrating examples of positions of X-ray sources in accordance with one aspect of the present invention. In the example of FIG. 3A, a projection radiographic system 300 has a first x-ray source 302 positioned at point A and a second x-ray source 304 positioned at point A'. Both X-ray sources 302 and 304 are affixed to and from a part of a rotor 305 which rotates within a limited range around an object 306 in an inspection tunnel 307 so that X-ray sources 302 and 304 are moved to positions B and B' as illustrated in FIG. 3B. X-ray source 302 may thus oscillate about object 306 between position A and A' and X-ray source 304 may thus oscillate about object 306 between position B and B'.

The limited range of movement of electromagnetic sources around an object depends on the number of electromagnetic sources. For example, in a projection radiographic system having two electromagnetic sources, such as the one illustrated in FIGS. 3A and 3B, the full limited range of the rotation angle of the x-ray sources would be 90 degrees so that all possible locations for explosives in an object are examined.

While object 306 moves through inspection tunnel 307, sources 302 and 304 along with their respective sensors oscillate back and forth within their respective limited range. The total combined limited range of both x-ray sources should equal 180 degrees for optimal detection range. The projected views stay in fixed relation to each other and cover several views of any material in object 306. The maximum moving mechanism speed and the minimum projection length of material 306 determine the oscillation frequency of sources 302 and 304 and their corresponding sensors. During the examination, sources 302 and 304 along with their corresponding sensors and screens may rotate at least one full respective limited range to assure at least one optimal view of object 306. However, it can be generalized that the oscillation frequency of sources and sensors correlates with the maximum moving mechanism speed and is inversely related to the minimum projection length of a material in object 306.

That is, if the conveyor belt has a relatively high speed, X-ray sources 302 and 304 along with their sensors must oscillate faster to capture as many slice images of the material in object 306. Conversely, if a conveyor belt has a relatively low speed, the X-ray sources and sensors can oscillate at a slower rate because they have "more time" to capture slice images of the material in object 306 to assure at least one optimal view. As for the minimum projection length of the material in object 306, a "thicker" material would allow sensors 302 and 304 to capture the projected image of the material more easily. As the minimum projection length of the material increases, the oscillation frequency of the sources 308 and 310 and sensors 312 and 314 decreases.

Figure 4A:
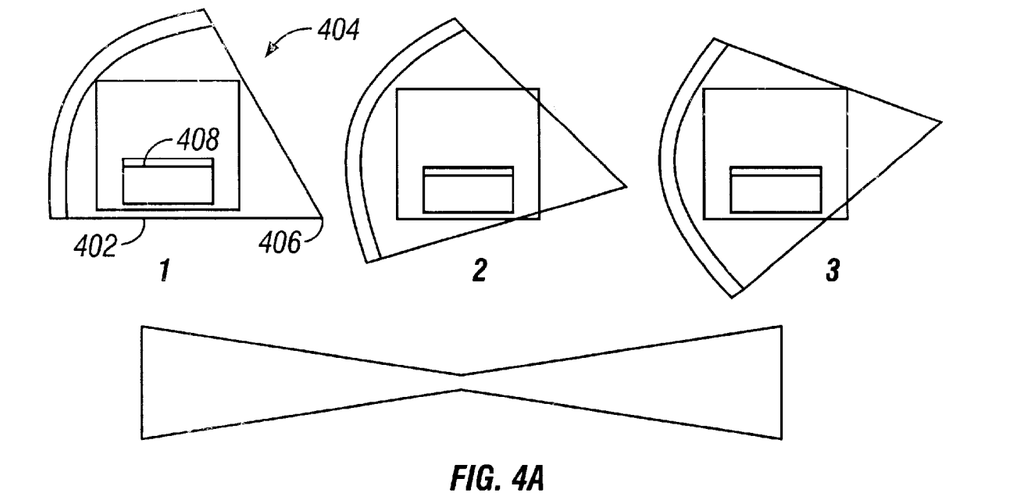
FIG. 4A is a schematic diagram of a side view of a projection radiographic system illustrating an example of a detection range based on the projected images of the object in accordance with one aspect of the present invention.
Figure 4B:
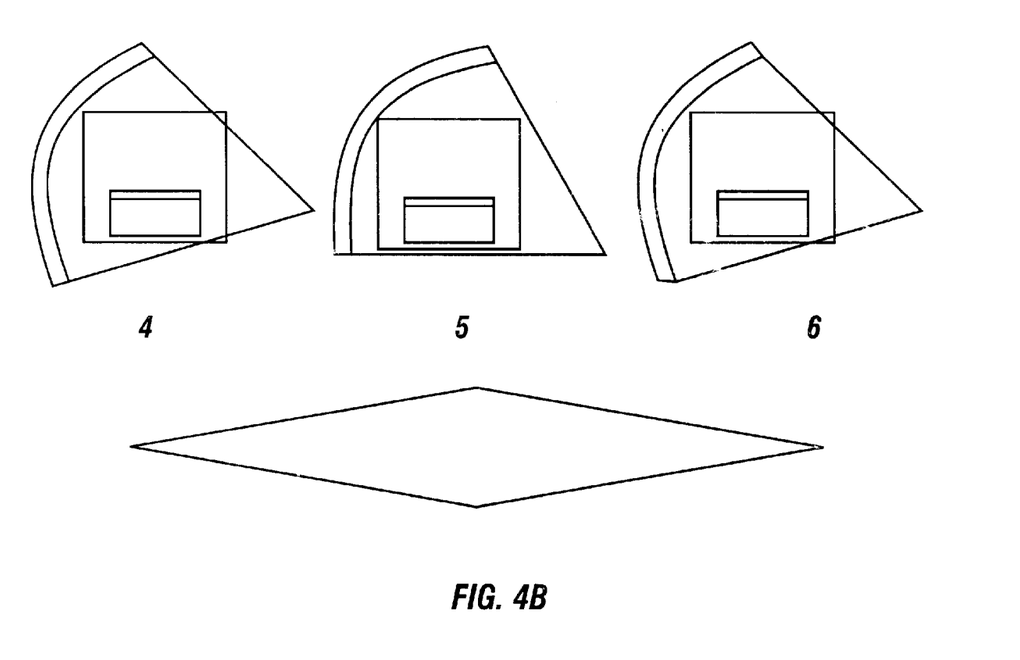
FIG. 4B is a schematic diagram of a side view of a projection radiographic system illustrating another example of a detection range based on the projected images of the object in accordance with one aspect of the present invention.

FIGS. 4A and 4B are schematic diagrams of a side view of a projection radiographic system illustrating examples of a detection range based on the projected images of an object in accordance with one aspect of the present invention. In the examples of FIG. 4A and FIG. 4B, positions 1 through 6 illustrate examples of different positions of x-ray sources and sensors. As the x-ray sources and sensors oscillate around a parcel 402 inside a projection radiographic system 404, the relative position of a source beam 406 to the thickness of a sheet of explosives 408 in object 402 varies. The range of the beam from source 406 defines the regions of accurate detection. In FIG. 6A, x-ray source 406, in positions 1 and 3, exposes thin sheet of explosives 408. However, the density projection spreads out and is overwhelmed by clutter in object 402. The accuracy of detection increases as the beam of x-ray source 406 is lined up to a very small angle relative to sheet of explosives 408 as shown in position 2 of FIG. 4A. Position 2 illustrates the optimal position of x-ray source 406 for the best resolution. FIG. 4B illustrates another example of a good detection region when x-ray source 406 is in positions 4 and 6 since the beam is lined up with the length of sheet of explosives 408.

Once projection radiographic system 404 acquires the projected images from the sensors, a limited view reconstruction technique can be used to approximate a three-dimensional model of the parcel content. Using limited view reconstruction techniques, the system can approximate the three-dimensional model of the parcel content while the conveyor moves at full speed, for example 500 mm per second. The sheet of explosives can be detected by its characteristic appearance and further confirmed by its signature character within the "good detection region."

Figure 5:
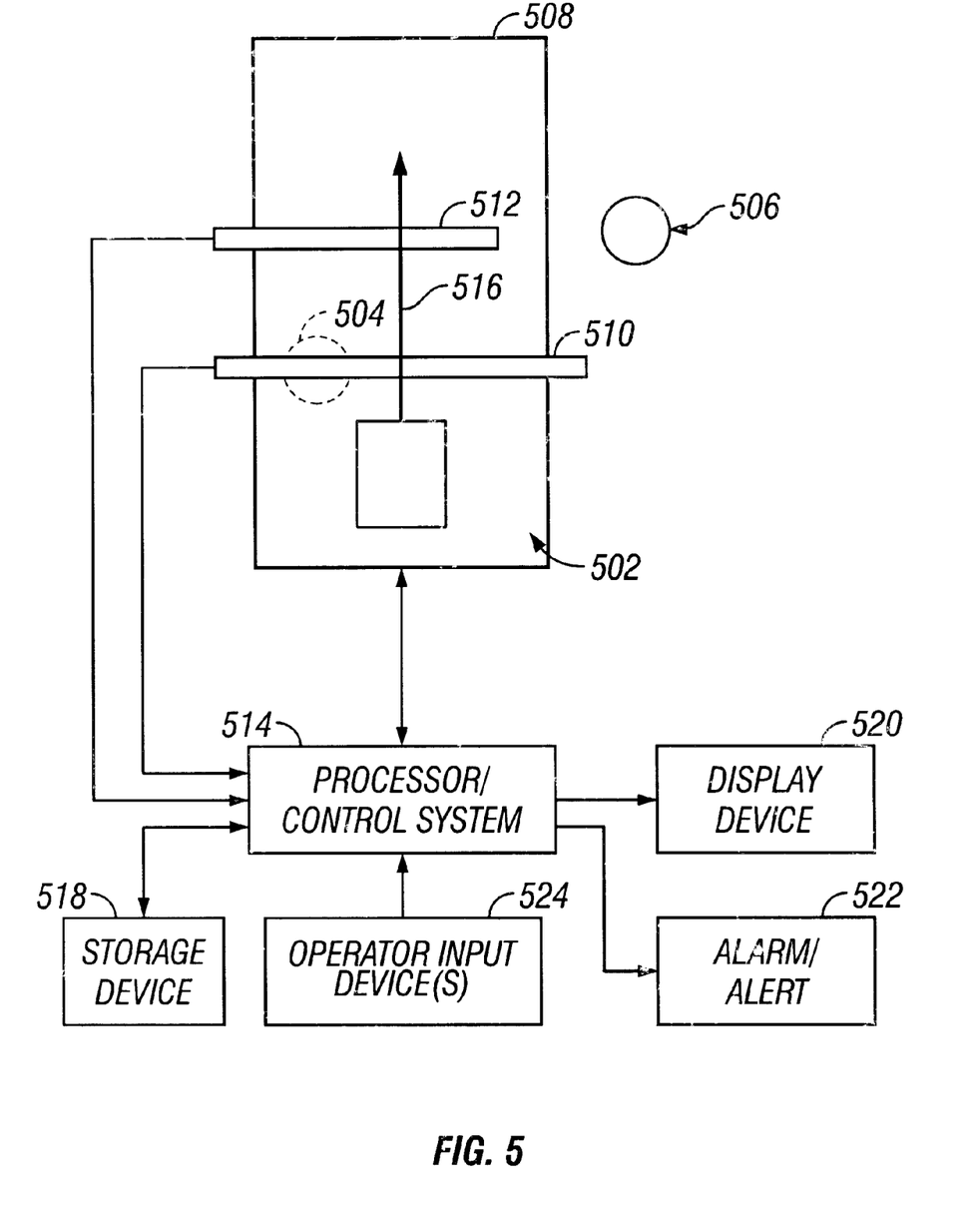
FIG. 5 is a schematic of a top view of a projection radiographic system in accordance with one aspect of the present invention.

FIG. 5 is a schematic of a top view of an object 502 being scanned by a projection radiographic system in accordance with one aspect of the present invention. In the example of FIG. 5, the projected images of a parcel 502 are supplied to a control system 514 for generating a reconstructed three-dimensional image of the content of parcel 502. The two x-ray sources 504 and 506 oscillate within their respective limited range around parcel 502 as parcel 502 travels in direction 516 across both x-ray sources 504 and 506 on top of a conveyor belt 508. Sensors 510 and 512, opposite to x-ray sources 504 and 506, respectively, capture the projected images of the content of parcel 502 and transmit the data to control system 514. A processor or several processors, within the control system 514 connected with the sensors 510, 512, receive and process the data from the sensors using a limited view reconstruction technique to generate a three-dimensional image of the content of parcel 502. A storage device 518, such as a hard drive, within the control system stores the data received from the sensors 510, 512 and data of specified physical characteristics of contraband, for example the density of explosives and drugs. The processed three-dimensional images of the content of parcel 502 are examined using data from the specified physical characteristic of contrabands stored in the storage device 518 to detect the presence of contraband or explosives in parcel 502. A display device 520, such as a monitor or television screen, is used to display the processed three-dimensional image of the content of parcel 502. In the event potential explosives are detected in parcel 502, an operator is alerted visually and optionally through sounds, such as an alarm 522. A flashing light or a noticeable visual display may be used to capture the operator's attention.

Upon the alert, the operator may examine closely the display device 520 and control the display of the processed image for confirmation. The operator may also choose to re-examine the content of parcel 502 by controlling the speed and direction of conveyor belt 508 via means of an input device, such as a mouse and a keyboard 524.

Figure 6:
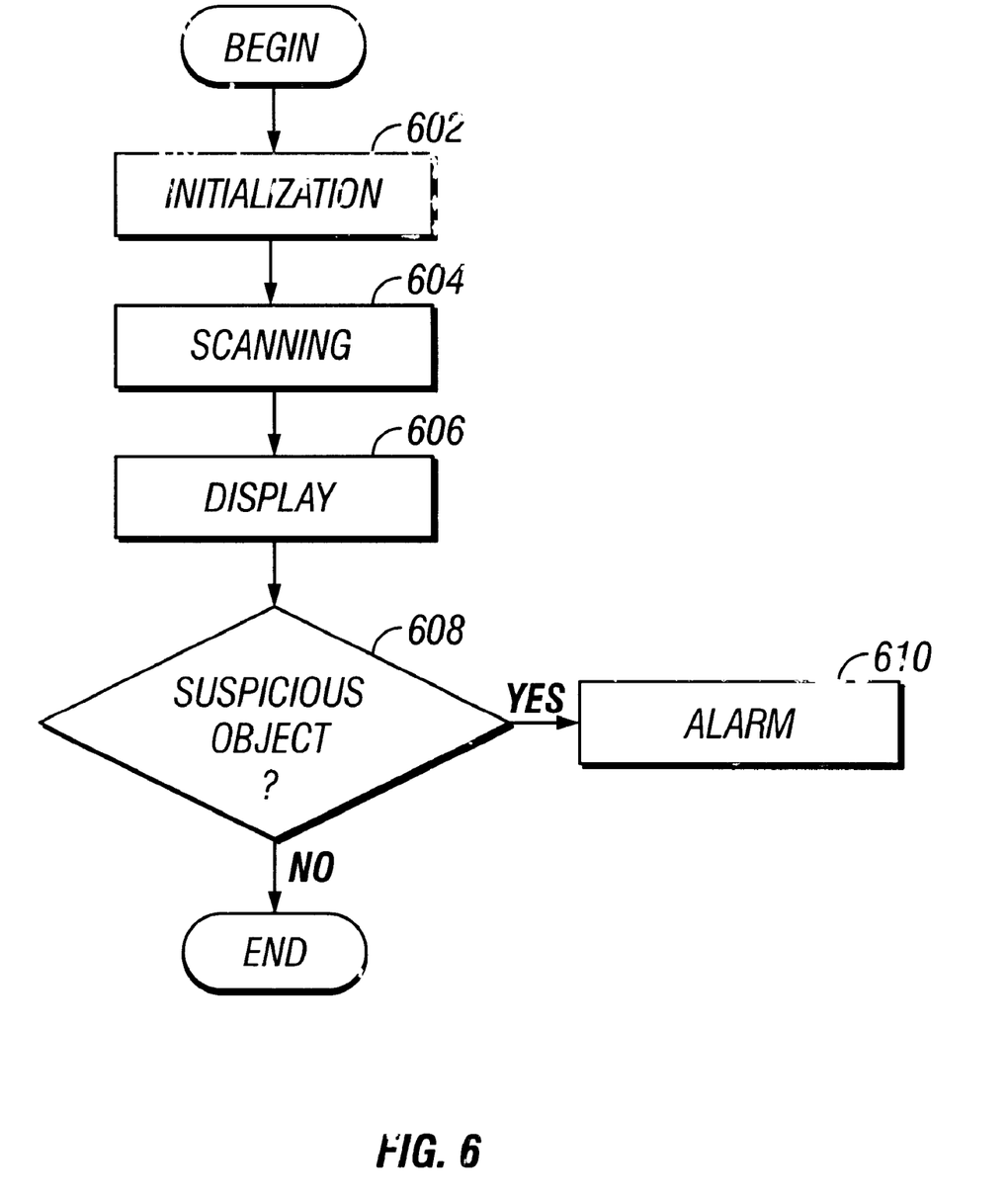
FIG. 6 is a flow diagram of an overview of the process in accordance with one aspect of the present invention.

FIG. 6 is a flow diagram of an overview of a process in accordance with one aspect of the present invention. In a first block 602, the projection radiographic system is initialized. Once the x-rays and sensors are positioned and initialized, the projection radiographic system starts scanning an object in block 604. The result of the scanning process is displayed in block 606. In block 608, based on the produced image and results, a control system helps determine whether the object may contain suspicious material. An alarm in block 610 is activated once the control system determines suspicious material.

Figure 7:
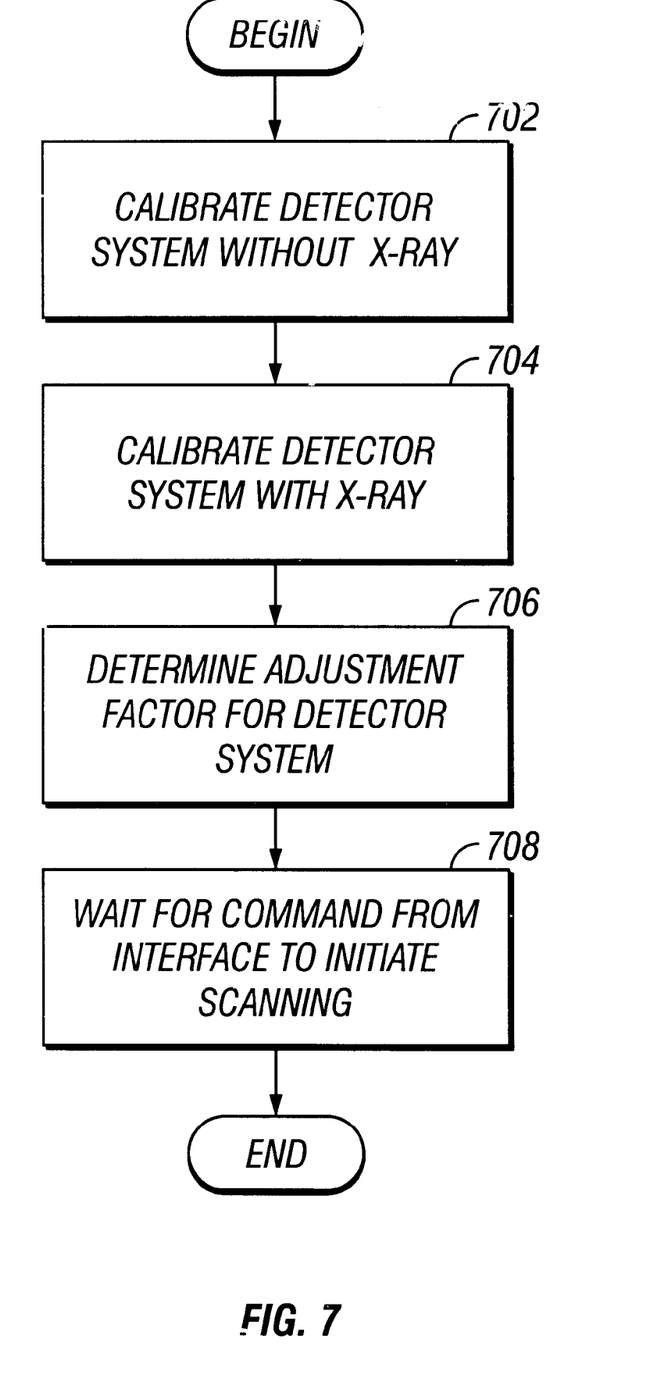
FIG. 7 is a flow diagram of the initialization process in accordance with one aspect of the present invention.

FIG. 7 is a flow diagram of an initialization as specified in block 602 of FIG. 6. The detector system (i.e. the screens and sensors) is first calibrated without the x-ray sources in block 702. The detector system is then calibrated with the x-ray sources in block 704. Based on both calibrations in block 702 and block 704, an adjustment factor for detector system is determined in block 706. The calibration process stops in block 708 to wait for a command from an interface to initiate the scanning.

Figure 8:
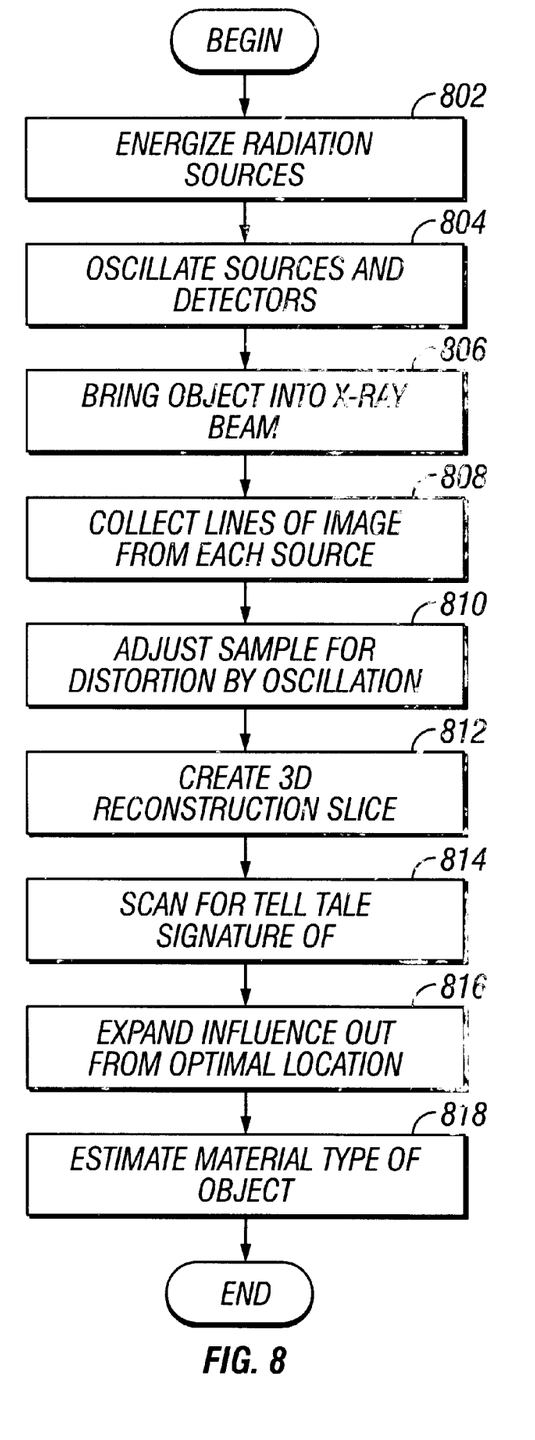
FIG. 8 is a flow diagram of the scanning process in accordance with one aspect of the present invention.

FIG. 8 is a flow diagram of a scanning process as specified in block 604 of FIG. 6. Once the scanning system is initialized, the radiation sources, i.e. the x-ray sources, are energized creating x-ray beams in block 802. The x-ray sources along with their corresponding detectors oscillate around the scanning tunnel in block 804. The object to be scanned is then brought into the x-ray beam of x-ray sources in block 806. Each x-ray source produces a line of image that is captured by each detector in block 808. The collected sample is then adjusted for distortion by the oscillating movement of the x-ray sources in block 810. In block 812, a three-dimensional reconstruction slice is created based on the matching data line from each source. In block 814, the scanning system scans for telltale signature of sheet of explosives. The system then expands its influence out from the optimal location of the telltale signature in block 816. As the number of data lines reaches some predetermined value, the system begins to estimate the material type of the object by background material subtraction in block 818.

Figure 9:
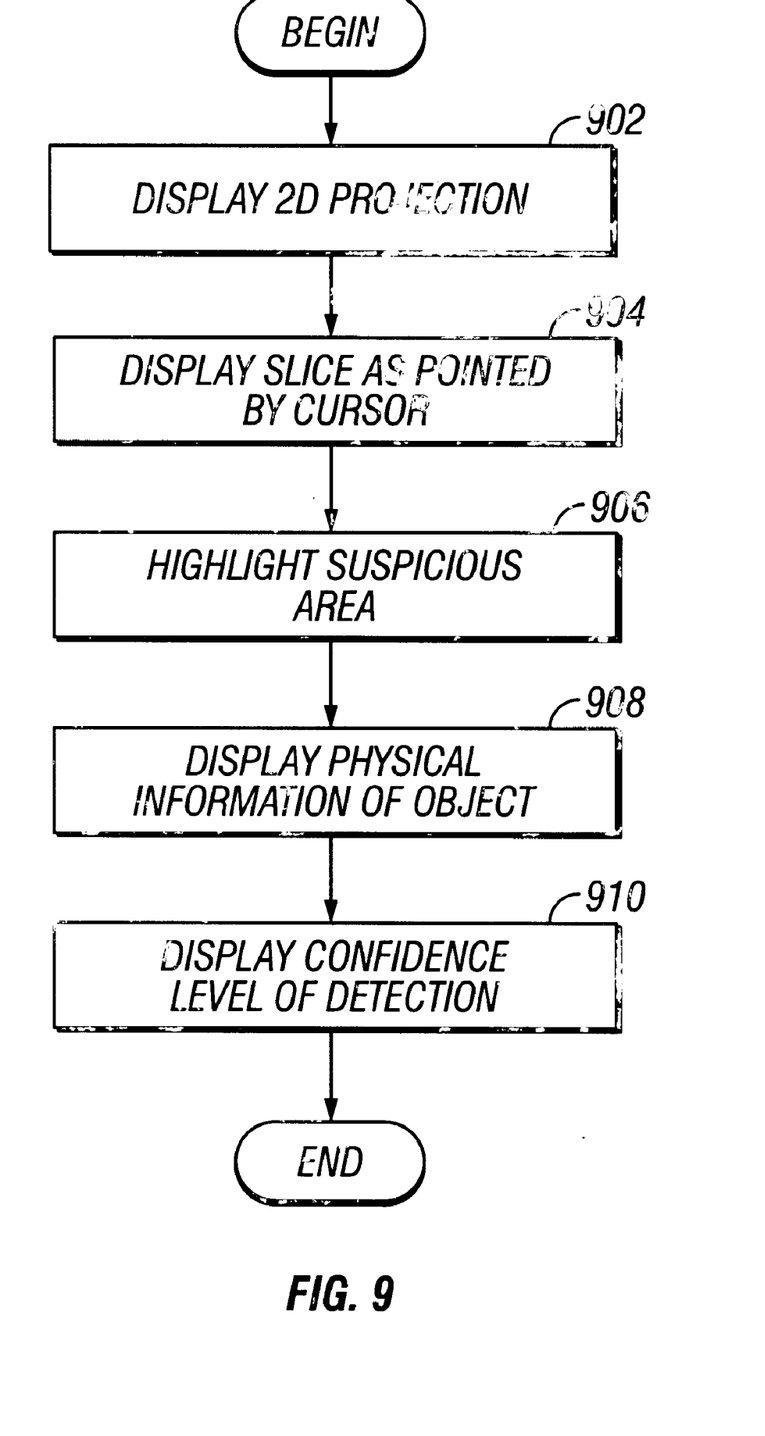
FIG. 9 is a flow diagram of the display process in accordance with one aspect of the present invention.

FIG. 9 is a flow diagram of a display process as specified in block 606 of FIG. 6. In a first block 902, a two-dimensional image projection is displayed on a screen such as a monitor. A cursor allows an operator to display a view of the captured slice of the object in block 904. The scanning system may also highlight suspicious areas for an operator to further investigate in block 906. Based on the resulting capture image, the scanning system displays physical information of the object in block 908. A display of confidence level of detection accompany the display of block 908 in block 910.

A limited three-dimensional reconstruction technique is used to create a three-dimensional reconstructed image of the content of the parcel based on the data captured by the sensors. The resulting image is shown using a display device such as a monitor or television. A control system examines the three-dimensional reconstructed image for a specified physical characteristic, such as the density or shape of explosives, in the parcel. In the event that there are potential explosives in the parcel, an operator is alerted through visual and audio cues, such as alarms and flashing lights as specified in block 610 of FIG.6. Otherwise, the parcel leaves the projection radiation system.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. A method for determining a specified physical characteristic of an object, the method comprising:

conveying the object through a scanning apparatus;

exposing the object to electromagnetic radiation from at least two sources of electromagnetic radiations, the at least two sources of electromagnetic radiation being relatively fixed to one another;

rotating the at least two sources of electromagnetic radiation in an oscillating pattern about the object, the oscillating pattern covering no more than 90 degrees of rotation about the object; and capturing projected radiation images of the object with electromagnetic radiation sensors responsive to the sources of electromagnetic radiation about the object.

2. The method according to claim 1 further comprising creating a reconstructed image of the object from said captured images.

3. A method for determining a specified physical characteristic of an object, the method comprising:

conveying the object through a scanning apparatus;

oscillating a scanner about the object in a rotation range of no more than 90 degrees, the scanner having at least two sources of electromagnetic radiation held in fixed angular relationship and corresponding electromagnetic sensor arrays positioned to received electromagnetic radiation from corresponding sources;

exposing the object with electromagnetic radiation while oscillating; and capturing with said sensor arrays projected radiation images of the object at a plurality of angular positions in the rotational range.

4. The method according to claim 3 further comprising creating a reconstructed image of the object from said captured images.

5. The method according to claim 1 further comprising providing an alert when said specified physical characteristic is detected in the object.

6. The method according to claim 2 further comprising providing an alert when said specified physical characteristic is detected in the object.

7. The method according to claim 3 further comprising providing an alert when said specified physical characteristic is detected in the object.

8. The method according to claim 4 further comprising providing an alert when said specified physical characteristic is detected in the object.

9. The method according to claim 1 wherein said specified physical characteristic is a density.

10. The method according to claim 2 wherein said specified physical characteristic is a density.

11. The method according to claim 3 wherein said specified physical characteristic is a density.

12. The method according to claim 4 wherein said specified physical characteristic is a density.

13. The method according to claim 1 wherein said specified physical characteristic is a shape.

14. The method according to claim 2 wherein said specified physical characteristic is a shape.

15. The method according to claim 3 wherein said specified physical characteristic is a shape.

16. The method according to claim 4 wherein said specified physical characteristic is a shape.

17. The method according to claim 1 wherein said specified physical characteristic is the presence of explosives.

18. The method according to claim 2 wherein said specified physical characteristic is the presence of explosives.

19. The method according to claim 3 wherein said specified physical characteristic is the presence of explosives.

20. The method according to claim 4 wherein said specified physical characteristic is the presence of explosives.

21. The method according to claim 1 wherein said specified physical characteristic is the presence of drugs.

22. The method according to claim 2 wherein said specified physical characteristic is the presence of drugs.

23. The method according to claim 3 wherein said specified physical characteristic is the presence of drugs.

24. The method according to claim 4 wherein said specified physical characteristic is the presence of drugs.

25. The method according to claim 1 wherein said electromagnetic radiation comprises x-rays.

26. The method according to claim 2 wherein said electromagnetic radiation comprises x-rays.

27. The method according to claim 3 wherein said electromagnetic radiation comprises x-rays.

28. The method according to claim 4 wherein said electromagnetic radiation comprises x-rays.

29. An apparatus for determining a specified physical characteristic of an object, the apparatus comprising:
- means for conveying the object through a scanning apparatus;
- means for exposing the object to electromagnetic radiation from at least two sources of electromagnetic radiation, the at least two sources of electromagnetic radiation being relatively fixed to one another;
- means for rotating the at least two sources of electromagnetic radiation in an oscillating pattern about the object, the oscillating pattern covering no more than 90 degrees of rotation about the object; and
- means for capturing projected radiation images of the object with electromagnetic radiation sensors responsive to the sources of electromagnetic radiation.

30. The apparatus according to claim 29 further comprising means for creating a reconstructed image of the object from said captured images.

31. An apparatus for determining a specified physical characteristic of an object, the apparatus comprising:
- means for conveying the object through a scanning apparatus;
- means for oscillating a scanner about the object in a rotation range of no more than 90 degrees, the scanner having at least two sources of electromagnetic radiation held in fixed angular relationship and corresponding electromagnetic sensor arrays positioned to received electromagnetic radiation from corresponding sources;
- means for exposing the object with electromagnetic radiation while oscillating; and
- means for capturing with said sensor arrays projected radiation images of the object at a plurality of angular positions in the rotational range.

32. The apparatus according to claim 31 further comprising means for creating a reconstructed image of the object from said captured images.

33. The apparatus according to claim 29 further comprising providing an alert when said specified physical characteristic is detected in the object.

34. The apparatus according to claim 30 further comprising providing an alert when said specified physical characteristic is detected in the object.

35. The apparatus according to claim 31 further comprising providing an alert when said specified physical characteristic is detected in the object.

36. The apparatus according to claim 32 further comprising providing an alert when said specified physical characteristic is detected in the object.

37. The apparatus according to claim 29 wherein said specified physical characteristic is a density.

38. The apparatus according to claim 30 wherein said specified physical characteristic is a density.

39. The apparatus according to claim 31 wherein said specified physical characteristic is a density.

40. The apparatus according to claim 32 wherein said specified physical characteristic is a density.

41. The apparatus according to claim 29 wherein said specified physical characteristic is a shape.

42. The apparatus according to claim 30 wherein said specified physical characteristic is a shape.

43. The apparatus according to claim 31 wherein said specified physical characteristic is a shape.

44. The apparatus according to claim 32 wherein said specified physical characteristic is a shape.

45. The apparatus according to claim 29 wherein said specified physical characteristic is the presence of explosives.

46. The apparatus according to claim 30 wherein said specified physical characteristic is the presence of explosives.

47. The apparatus according to claim 31 wherein said specified physical characteristic is the presence of explosives.

48. The apparatus according to claim 32 wherein said specified physical characteristic is the presence of explosives.

49. The apparatus according to claim 29 wherein said specified physical characteristic is the presence of drugs.

50. The apparatus according to claim 30 wherein said specified physical characteristic is the presence of drugs.

51. The apparatus according to claim 31 wherein said specified physical characteristic is the presence of drugs.

52. The apparatus according to claim 32 wherein said specified physical characteristic is the presence of drugs.

53. The apparatus according to claim 29 wherein said electromagnetic radiation comprises x-rays.

54. The apparatus according to claim 30 wherein said electromagnetic radiation comprises x-rays.

55. The apparatus according to claim 31 wherein said electromagnetic radiation comprises x-rays.

56. The apparatus according to claim 32 wherein said electromagnetic radiation comprises x-rays.

57. An apparatus for scanning an object for the presence of a specified physical characteristic, the apparatus comprising:
- a conveyor conveying the object through the apparatus along a path;
- a rotor mounted to rotationally oscillate in an arc of no more than 90 degrees about the path;
- a pair of sources of electromagnetic radiation mounted to said rotor;
- a plurality of electromagnetic radiation sensors arranged to capture electromagnetic radiation emanating from said pair of sources and passing through the object; and
- a processor for receiving signal from said sensors.

58. An apparatus according to claim 57, further comprising a display for displaying a reconstructed three-dimensional image of said object.

59. An apparatus for scanning an object for the presence of a specified physical characteristic, the apparatus comprising:
- a conveyor conveying the object through the apparatus along a path;
- a rotor mounted to rotationally oscillate in an arc of no more than 90 degrees about the path;
- a pair of sources of electromagnetic radiation mounted to said rotor;
- a plurality of electromagnetic radiation sensor arrays mounted to said rotor to receive electromagnetic radiation from corresponding sources of electromagnetic radiation; and
- a processor for receiving signal from said sensors.

60. An apparatus according to claim 59, further comprising a display for displaying a reconstructed three-dimensional image of said object.

61. A program storage device readable by a machine, tangibly embodying a program of instructions readable by the machine to perform a method generating a reconstructed three-dimensional view of an object based on a limited number of x-ray projections, the method comprising:

conveying the object through a scanning apparatus;

exposing the object to electromagnetic radiation from at least two sources of electromagnetic radiation, the at least two sources of electromagnetic radiation being relatively fixed to one another;

rotating the at least two sources of electromagnetic radiation in an oscillating pattern about the object, the oscillating pattern covering no more than 90 degrees of rotation about the object; and capturing projected radiation images of the object with electromagnetic radiation sensors responsive to the sources of electromagnetic radiation about the object.

62. The program storage device according to claim 61 wherein the method further comprises creating a reconstructed image of the object from said captured images.

63. A program storage device readable by a machine, tangibly embodying a program of instructions readable by the machine to perform a method for generating a reconstructed three-dimensional view of an object based on a limited number of x-ray projections, the method comprising:

conveying the object through a scanning apparatus;

oscillating a scanner about the object in a rotation range of no more than 90 degrees, the scanner having at least two sources of electromagnetic radiation held in fixed angular relationship and corresponding electromagnetic sensor arrays positioned to receive electromagnetic radiation from corresponding sources;

exposing the object with electromagnetic radiation while oscillating; and capturing with said sensor arrays projected radiation images of the object at a plurality of angular positions in the rotational range.

64. The program storage device according to claim 63 wherein the method further comprises creating a reconstructed image of the object from said captured images.

* * * * *

UNITED STATES PATENT AND TRADEMARK OFFICE
CERTIFICATE OF CORRECTION

PATENT NO. : 6,473,487 B1
DATED : October 29, 2002
INVENTOR(S) : Khai Minh Le It is certified that error appears in the above-identified patent and that said Letters Patent is hereby corrected as shown below:

Column 1,
Line 39, remove the word "ray"

Signed and Sealed this

Twenty-third Day of September, 2003

JAMES E. ROGAN
*Director of the United States Patent and Trademark Office*